United States Patent [19]
Hasida et al.

[11] Patent Number: 6,127,137
[45] Date of Patent: Oct. 3, 2000

[54] ACIDIC PHOSPHOLIPASE, PRODUCTION AND METHODS USING THEREOF

[75] Inventors: Miyoko Hasida; Noriko Tsutsumi, both of Chiba-ken, Japan; Torben Halkier, Birkerod; Mary Ann Stringer, Copenhagen, both of Denmark

[73] Assignee: Novo Nordisk A/S, Bagsvaerd, Denmark

[21] Appl. No.: 09/295,186

[22] Filed: Apr. 20, 1999

Related U.S. Application Data

[63] Continuation of application No. PCT/DK97/00490, Oct. 30, 1997.

[30] Foreign Application Priority Data

Oct. 31, 1996 [DK] Denmark .................................. 1215/96

[51] Int. Cl.⁷ ............................... C12Q 1/34; C12N 9/18; C12N 1/14
[52] U.S. Cl. .......................... 435/18; 435/197; 435/254.1
[58] Field of Search .................................. 435/197, 254.1, 435/18

[56] References Cited

FOREIGN PATENT DOCUMENTS 0 513 709  11/1992  European Pat. Off. .
0 622 446  11/1994  European Pat. Off. .

OTHER PUBLICATIONS

Oishi et al Biosci. Biotech. Biochem., vol. 60, No. 7, pp. 11087–1092 (1996).
Kawasaki et al J. Biochem., vol. 77, pp. 1233–1244 (1975).
Masuda et al. Eur. J. Biochem, vol. 202, pp. 183–187 (1991).
Ichimasa et al. Agric. Biol. Chem., vol. 49, No. 4, pp. 1083–1089 (1985).
Lee et al. The Journal of Biological Chemistry, vol. 269, No. 31, pp. 19725–19730 (1994).
Kuwabara et al. Agric. Biol. Chem., vol. 52, No. 10, pp. 2451–2458 (1988).

*Primary Examiner*—Elizabeth Slobodyansky
*Attorney, Agent, or Firm*—Steve T. Zelson; Valeta A. Gregg

[57] ABSTRACT

An acidic phospholipase is obtained from a strain of the genus Hyphozyma. It is able to hydrolyze both fatty acyl groups in intact phospholipid. Advantageously, it has no lipase activity and is active at very low pH; these properties make it very suitable for use in oil degumming, as enzymatic and alkaline hydrolysis (saponification) of the oil can both be suppressed. The phospholipase is not membrane bound, making it suitable for commercial production and purification.

15 Claims, 7 Drawing Sheets

```
              190       200       210       220       230       240
               |    o    |    o     o   ooooo   |  o||ooooo  |  o||   oo  ||
Hyphozyma      GFDGRNETANQRG-TGGLLQLAEYIAGLSGGSWATASLTMNNWATTQSLKD---N---IW
Saccharomyces  AMDNRTDGANEHG-LGGLLQGATYLAGLSGGNWLTSTLAWNNWTSVQAIVDNTTESNSIW
Torulaspora    AMDNRTDGANEHG-LGGLLQSTTYLAGLSGGNWLVGTLAWNNWTSVQDIVNNMTEDDSIW
Penicillium    AFDSRTDNATATGHLGGLLQSATYISGLSGGSWLLGSIYINNFTTVDKLQTHEAG--SVW
                                                            o
              250       260       270       280       290       300
               ||  o                           o   o|  o|  |o|o  o  |||
Hyphozyma      DLESNLIV-P------EDG-KVSFYASILAAVAGKRNEGYQTSLTDYFGLSIADKILNGSM
Saccharomyces  DISHSILT-P---DGINIFKTGSRWDDISDDVQDKDAGFNISLADVWGRALAYNFWPSLH
Torulaspora    DISNSIIN-P---GGFMIVTTIKRWDHISDAVEGKQDAGFNVSLTDIWGRALSYNFFPSLY
Penicillium    QFGNSIIEGPDAGGIQLLDSAGYYKDLADAVDGKKKAGFDTTLTDIWGRALSYQMFNASN 310       320       330       340       350       360
                oo                    o   o  oo    |o  |oo oo   |o  o|o|  oooo o o|  o
Hyphozyma      YGNKFSVEWSDVKNTSKFTDASMPFPIIADEREPGELIIPRNTTIWEFNPYEFGSWNPN
Saccharomyces  R-GGVGYTWSTLREADVFKNGEMPFPITVADGRYPGTTVINLNATLFEFNPFEMGSWDPT
Torulaspora    R-GGVAYTWSTLRDVEVFQNGEMPFPISVADGRYPGTQIIDLNATVFEFNPFEMGSWDPT
Penicillium    --GGLSYTWSSIADTPEFQDGDYPMPFVVADGRNPGELVIGSNSTVYEFNPWEFGTFDPT
```

FIG. 4b

```
                            370       380       390       400       410       420
                              |    oo |    o |       o| o||       oo||oo      o |  o
Hyphozyma      |     o |oo      |          o |                 o |                  o
               VSAFIPIEILGSSLDNGTSVLPDGVCVGGYETVAWVTGTSATLFSGLYLELISTSSNNII
Saccharomyces  LNAFTDVKYLGTNVTNG-KPVNKGQCIAGFDNTGFITATSSTLFNQFLLRLNSTDLPSFI
Torulaspora    LNAFTDVKYLGTKVSNG-EPVNKGQCVAGYDNTGFIMGTSSSLFNQFLQINSTSLPSFI
Penicillium    IFGFVPLEYLGSKFEGGSLPSNES-CIRGFDSAGFVIGTSSSLFNQFLLQINTTSLPSFI 430       440       450       460       470       480
                              o||   oooo          oo   o||       |oooo  o||o|oo
Hyphozyma      VDALKEIAQAVSNEQNDVSLV-PNPFYGYVG--EGDVQVSDLRNITLVDGGLDNENVPL
Saccharomyces  ANLATDFLEDLSDNSDDIAIYAPNPFKEANFLQKNATSSIIESEYLFLVDGGEDNQNIPL
Torulaspora    KNLVTGFLDDLSEDEDDIAIYAPNPFKDTSYIQDNFSKSISESDYLYLVDGGEDNQNIPL
Penicillium    KDVFNGILFDLDKSQNDIASYDPNPFYKYN----EHSSPYAAQKLLDVVDGGEDGQNVPL 490       500       510       520       530       540
               oo||  o |ooo o|o ooo    oo  o||o   o       oo |oo  o         o
Hyphozyma      WPLVEPARDLDVIIAIDSSADVTN-WPNASALYQTSLRAQYPTYSQ--YAFPVMPDTNTV
Saccharomyces  VPLLQKERELDVIFALDNSADTDDYWPDGASLVNTYQRQFGSQGLN--LSFPYVPDVNTF
Torulaspora    VPLVQDERNVDVIFALDNSADTDYWPDGASLVSTYERQFSSQGLN--MSFPYVPDKRTF
Penicillium    HPLIQPERHVDVIFAVDSSADTDYFWPNGTSLVATYERSLNSSGIANGTAFPAVPDQNTF
```

FIG. 4C

```
                            |o oo  |o o|oo|   o        o         o||oo|o      oo||
Hyphozyma         VNRGLNTRPVFYGCNATVNVTNADTSFNGTKTPIIVYMPSYPYAAFADTSTFKL------
Saccharomyces     VNLGLNKKPTFFGCDA-RNLTDLEYIP-----PLIVYIPNSRHSFNGNQSTFKMSYSDSE
Torulaspora       VNLGLADKPSFFGCDA-QNLTDLNYIP-----PLVVYIPNARHSYNSNTSTFKLSYTDDE
Penicillium       INLGLSTRPSFFGCDS-SNQTGPS--------PLVVYIPNAPYSYHSNISTFQLSTDDAE Hyphozyma         RLGMIKNGFEAATMGNFTDDSDFLGCVGCAIIRRKQQNLNATLPSECSQCFTNYCWNGTI
Saccharomyces     RLKMIKNGFEAATRGNLTDDSSFMGCVACAVMRRKQQSLNATLPEECSTCFTNYCWNGTI
Torulaspora       RDNIILNGYEVATMANSTLDDNWTACVACACAILSRSFERTGTTLPDICSQCFDRYCWNGTV
Penicillium Hyphozyma         DSRSVSGVGNDDYSSSASLSASAAAASASASASASASASGSSTHKKNAGNALVNYSNL
Saccharomyces     DDTPVSGLDNSDFDPTAASSAYSAYNTESYSSSSATGSKKNG------AG-----LPA
Torulaspora       N-------------STRPESYDPAFYLADNSMASVS------------------------L
Penicillium Hyphozyma
Saccharomyces     NTNTFIGVLSVISAVFGLI
Torulaspora       TPTSFTSILTLLTAIAGFL
Penicillium       PTMLSTVVAAGLAMLILV-
```

FIG. 4d

ACIDIC PHOSPHOLIPASE, PRODUCTION AND METHODS USING THEREOF

CROSS-REFERENCE TO RELATED APPLICATIONS

This application is a continuation application of PCT/DK97/00490 filed Oct. 30, 1997 and claims priority under 35 U.S.C. 119 of Danish application 1215/96 filed Oct. 31, 1996, the contents of which are fully incorporated herein by reference.

TECHNICAL FIELD

This invention relates to a novel phospholipase, DNA encoding it and to its production and use.

BACKGROUND ART

Phospholipids, such as lecithin or phosphatidylcholine, consist of glycerol esterified with two fatty acids in an outer (sn-1) and the middle (sn-2) positions and esterified with phosphoric acid in the third position; the phosphoric acid, in turn, may be esterified to an amino-alcohol. Phospholipases are enzymes which participate in the hydrolysis of phospholipids. Several types of phospholipase activity can be distinguished, including phospholipase A1 and A2 which hydrolyze one fatty acyl group (in the sn-1 and sn-2 position, respectively) to form lysophospholipid; and lysophospholipase (or phospholipase B) which can hydrolyze the remaining fatty acyl group in lysophospholipid. This invention relates to a phospholipase that has the ability to hydrolyze both fatty acyl groups in a phospholipid. Enzymes with this activity are also some times called phospholipase B.

Enzymes with phospholipase B activity have been reported from various fungal sources, including *Penicillium notatum* (also known as *P. chrysogenum*; N. Kawasaki, J. Biochem., 77, 1233–44, 1975; N. Masuda et al., Eur. J. Biochem., 202, 783–787, 1991), *Saccharomyces cerevisiae* (M. Ichimasa et al., Agric. Biol. Chem., 49 (4), 1083–89, 1985; F. Paultauf et al., J. Biol. Chem., 269, 19725–30, 1994), *Torulaspora delbrueckii* (old name *Saccharomyces rosei*; Y. Kuwabara, Agric. Biol. Chem., 52 (10), 2451–58, 1988; FEMS, Microbiol. Letters, 124, 29–34), *Schizosaccharomyces pombe* (H. Oishi et al., Biosci. Biotech. Biochem., 60 (7), 1087–92, 1996), *Aspergillus niger* (Technical Bulletin, G-zyme™ G999, Enzyme Bio-Systems Ltd.) and *Corticium centrifugum* (S. Uehara et al., Agric. Biol. Chem., 43 (3), 517–525, 1979).

It is known to use phospholipase in, e.g., enzymatic oil degumming (U.S. Pat. No. 5,264,367, Metallgesellschaft, R ôhm), treatment of starch hydrolysate (particularly from wheat starch) to improve the filterability (EP 219,269, CPC International) and as an additive to bread dough to improve the elasticity of the bread (U.S. Pat. No. 4,567,046, Kyowa Hakko).

It is the object of this invention to provide an improved phospholipase for use in such processes.

STATEMENT OF THE INVENTION

The present inventors have found that an acidic phospholipase can be obtained from a strain of the genus Hyphozyma. It is able to hydrolyze both fatty acyl groups in intact phospholipid. Advantageously, it has no lipase activity and is active at very low pH; these properties make it very suitable for use in oil degumming, as enzymatic and alkaline hydrolysis (saponification) of the oil can both be suppressed. The phospholipase is not membrane bound, making it suitable for commercial production and purification.

WO 93/24619 (Novo Nordisk) discloses a lipase from Hyphozyma sp. LF-132 (CBS 648.91), but the production of phospholipase by this genus has never been reported. We have found that the phospholipase of this invention can be obtained from the same strain as the known lipase, and that the two enzymes can be separated.

Accordingly, a first aspect of the invention provides an isolated phospholipase which is able to hydrolyze both fatty acyl groups in a phospholipid, is derivable from a strain of Hyphozyma, and has optimum phospholipase activity at about 50° C. and pH 3 measured at the conditions described in Example 3.

The invention also provides an isolated phospholipase which is able to hydrolyze both fatty acyl groups in a phospholipid, and is a polypeptide comprising at its N-terminal a partial amino acid sequence which is the sequence shown in positions 1–497 of SEQ ID NO: 11, or is at least 50% identical therewith In another aspect, the invention provides an isolated phospholipase which is able to hydrolyze both fatty acyl groups in a phospholipid, and is a polypeptide containing amino acid sequences which are at least 50% identical with the amino acid sequences shown in SEQ ID NO: 1–8, disregarding Xaa.

The invention further provides an isolated DNA sequence which encodes said phospholipase.

Yet another aspect of the invention provides a method of producing a phospholipase, comprising cultivation of a phospholipase-producing strain of Hyphozyma in a suitable nutrient medium, followed by recovery of the phospholipase.

A further aspect of the invention provides a method for producing a phospholipase, comprising isolating a DNA sequence encoding the phospholipase from a phospholipase-producing strain of Hyphozyma, combining the DNA fragment with appropriate expression signal(s) in an appropriate vector, transforming a suitable heterologous host organism with the vector, cultivating the transformed host organism under conditions leading to expression of the phospholipase, and recovering the phospholipase from the culture medium.

The invention also provides use of said phospholipase in a process comprising treatment of a phospholipid or lysophospholipid with the phospholipase so as to hydrolyze fatty acyl groups.

Finally, the invention provides a process for reducing the content of phospholipid in a vegetable oil, comprising treating the oil with an aqueous dispersion of an acidic phospholipase at pH 1.5–3 so as to hydrolyze a major part of the phospholipid, and separating an aqueous phase containing the hydrolyzed phospholipid from the oil.

BRIEF DESCRIPTION OF DRAWINGS

FIG. 4a–d gives a comparison of SEQ ID NO: 11 with 3 prior-art sequences (SEQ ID NO:16–18).

DETAILED DISCLOSURE OF THE INVENTION

Phospholipase

The phospholipase of the invention is able to hydrolyze both acyl groups in a phospholipid molecule (such as phosphatidyl choline or lecithin) without intermediate accumulation of lysophospholipid and is also able to hydrolyze the fatty acyl group of a lysophospholipid (such as lysophosphatidyl choline or lyso-lecithin). Advantageously, the phospholipase of the invention is not membrane bound.

A preferred enzyme is derived from Hyphozyma sp. strain CBS 648.91. Its molecular weight is about 94 kDa by SDS, about 87 kDa by gel filtration, and 92 kDa by mass spectrometry. It is believed to be glycosylated. It has an isoelectric point of about 5.6. It has no lipase activity, i.e. it does not hydrolyze triglycerides.

Figure 1:
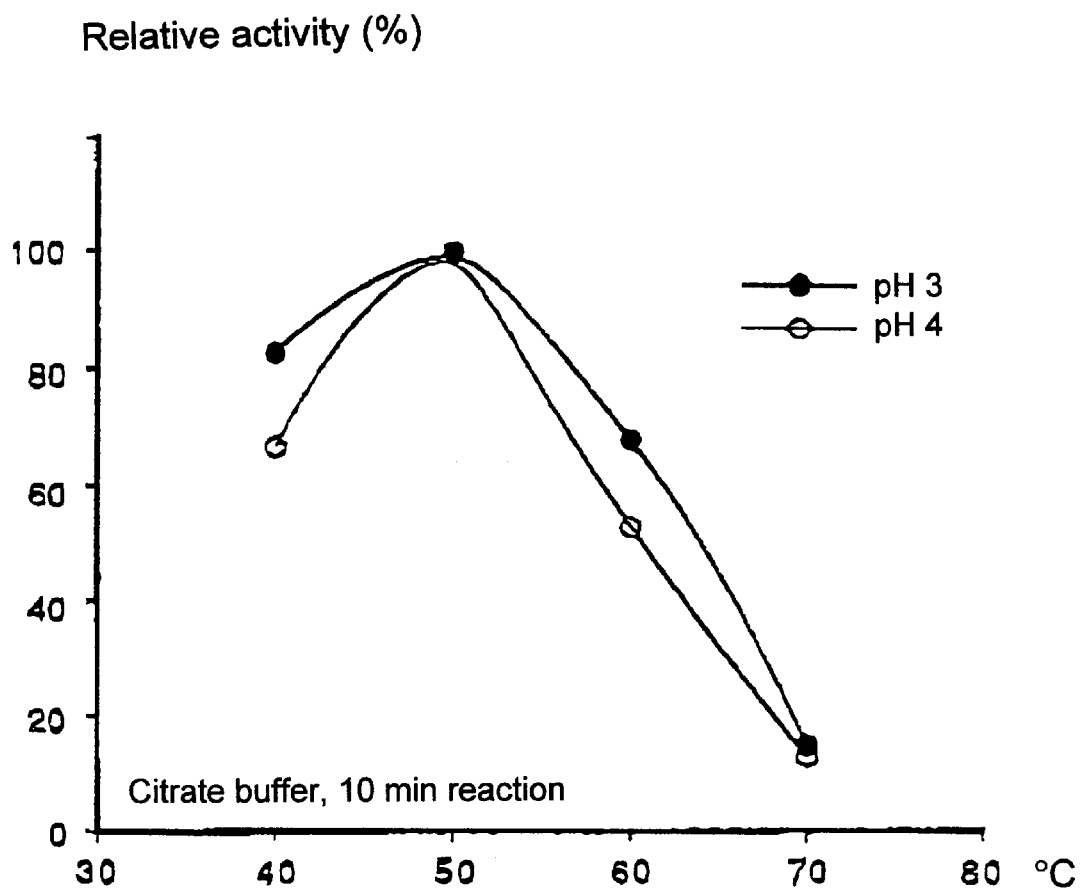
FIGS. 1, 2 and 3 show the temperature profile, pH profile and thermostability, respectively, of phospholipase from Hyphozyma sp. CBS 648.91. Further details are given in Example 3.
Figure 2:
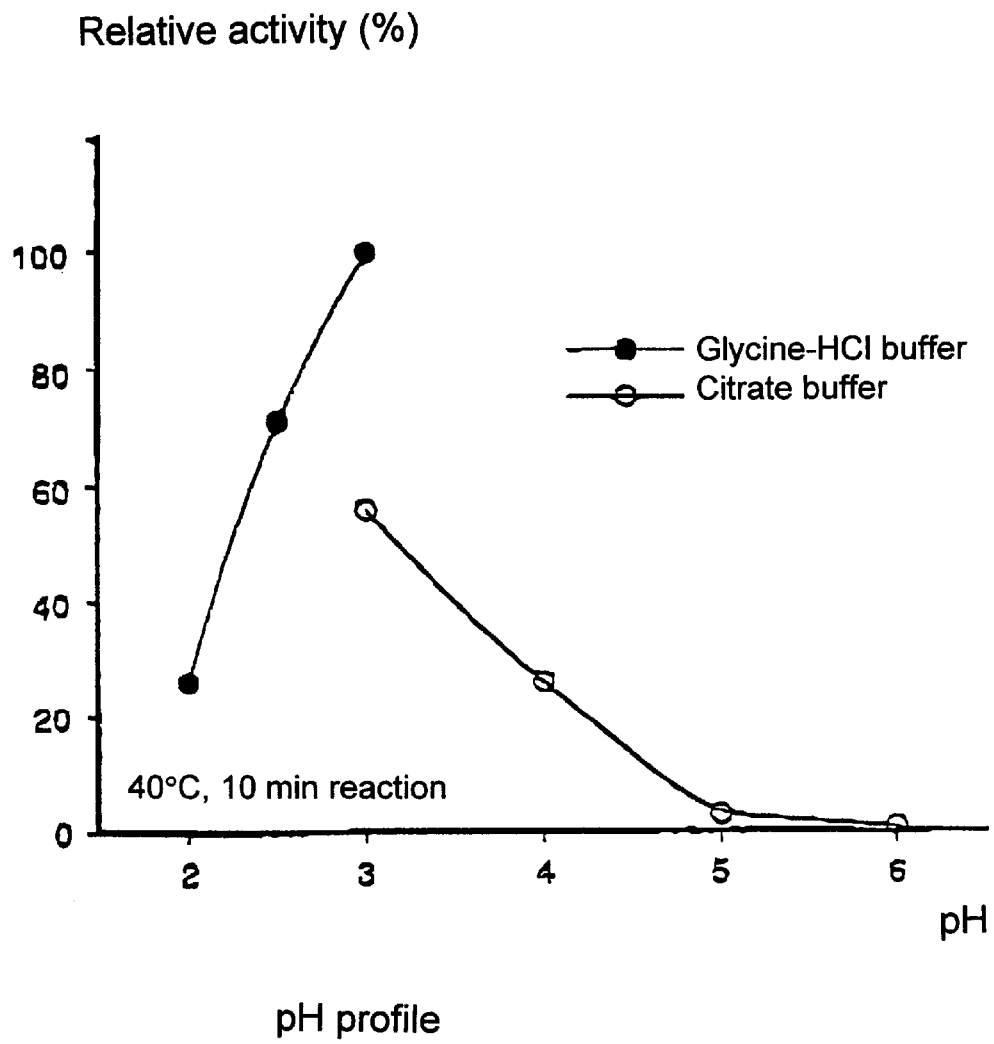

The influence of pH and temperature on the activity of this phospholipase is shown in FIG. 1 and 2. As shown in these figures, the enzyme has optimum activity at about pH 3 and 50° C.

Figure 3:
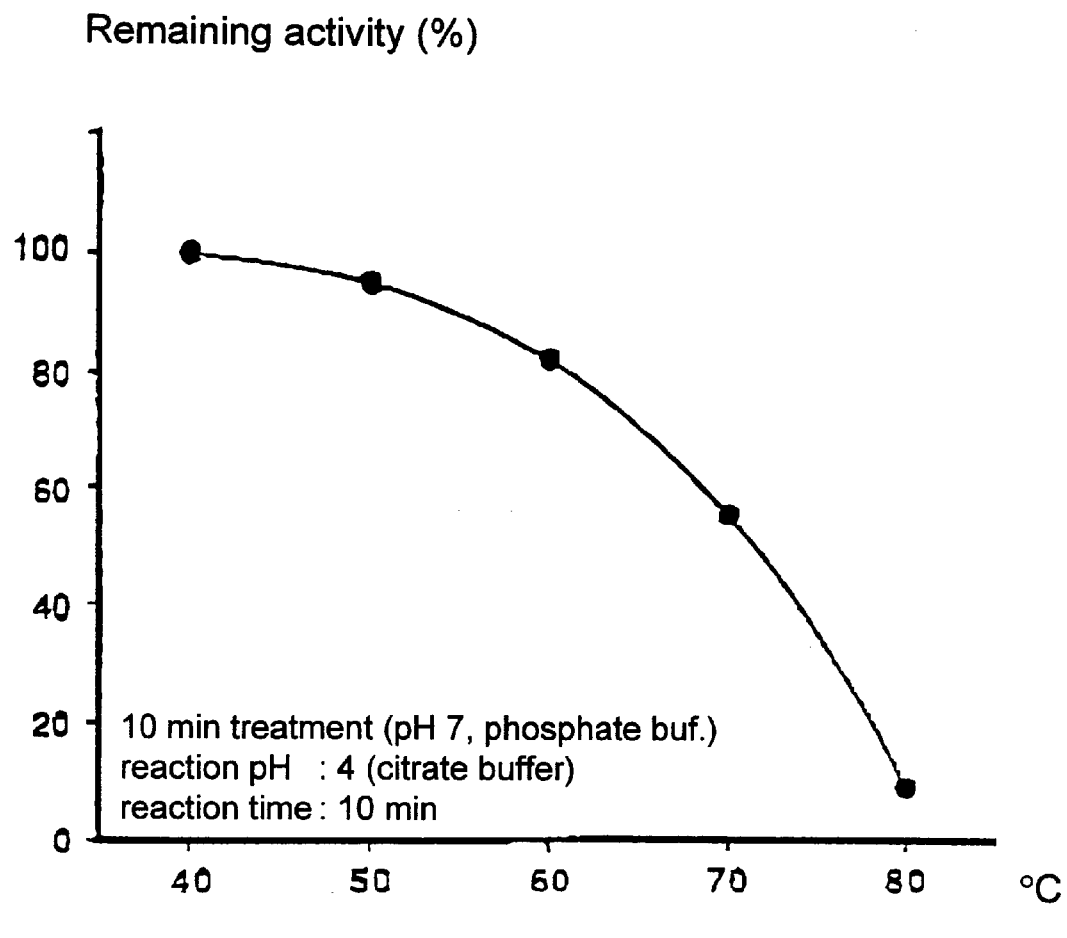
Figure 4A:
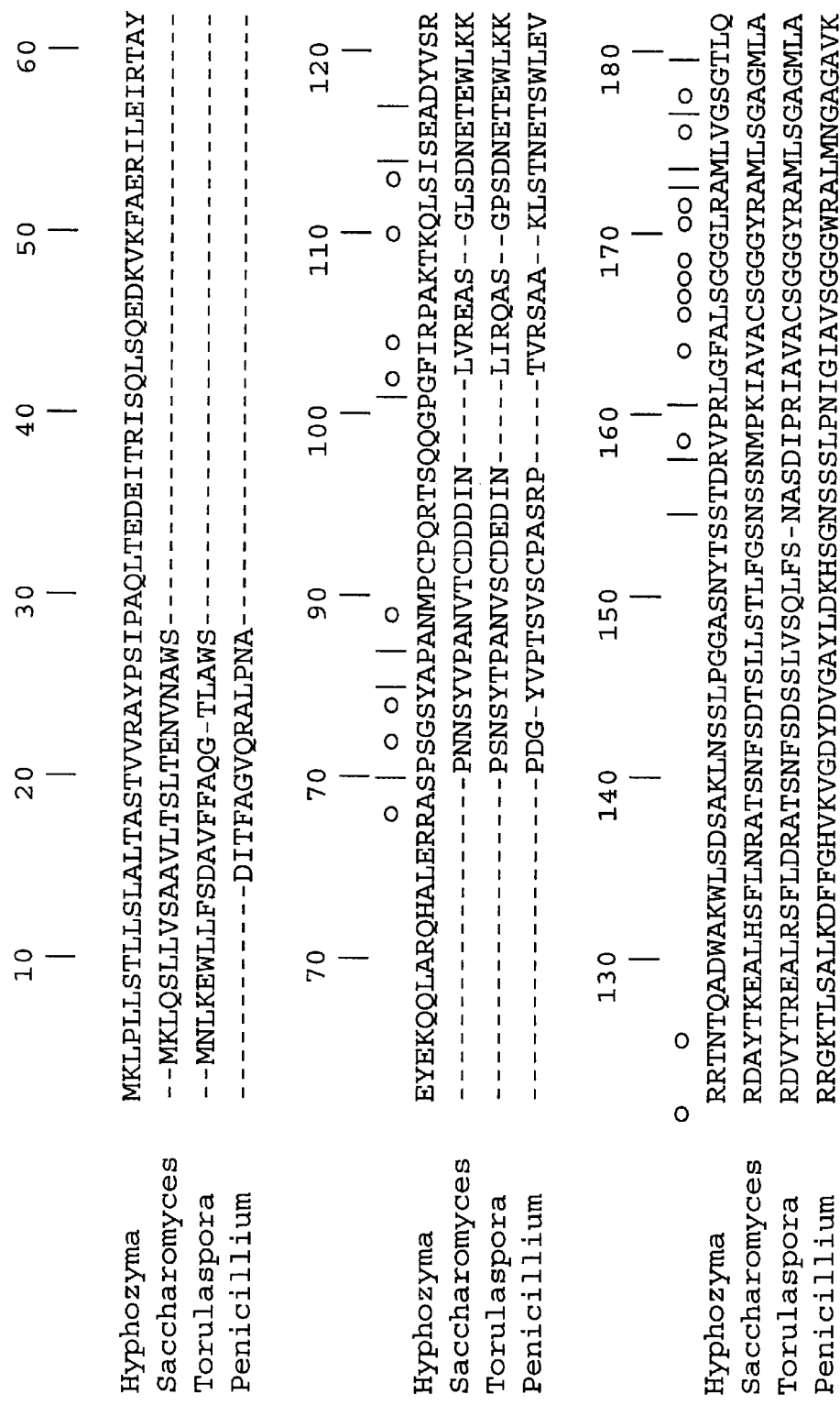

FIG. 3 shows the thermostability of this enzyme, expressed as the residual activity after 10 minutes at pH 7 at various temperatures. It is seen that the enzyme retains more than 90% activity at temperatures up to 50° C., more than 75% up to 60° C. and more than 50% up to 70° C.

Phospholipase Activity Assay

Two different units are used in this specification:

1 unit (phospholipase activity unit) is the amount of phospholipase that releases one $\mu$(micro)-mole of fatty acid per minute from DPPC (dipalmitoyl phosphatidylcholine) at 40° C. and pH 4. The amount of released fatty acid is determined by NEFA-C test Wako.

1 International Unit (IU) is the amount of phospholipase that releases one $\mu$(micro)-equivalent of free fatty acid per minute from egg yolk in the presence of calcium and deoxycholate at pH 8.0 and 40° C. in a pH-stat. The released fatty acids are titrated with 0.1 N sodium hydroxide and the base volume is monitored as a function of time.

Assay for Action Pattern of Phospholipase

The following test is used to identify if a given enzyme has the ability to hydrolyze both fatty acyl groups of a phospholipid without the accumulation of lysophospholipid.

A substrate solution is prepared containing 2% L-α (alpha)-phosphatidylcholine, dipalmitoyl (product of Wako Pure Chemical Industries Ltd.) and 2% Triton X-100. A buffer solution is prepared containing 0.4 M citrate buffer (pH 5). Enzyme solutions are prepared containing various amounts of the sample to be analyzed.

0.5 ml of the substrate solution, 0.25 ml of the buffer solution and 0.05 ml of 0.1 N $CaCl_2$ are mixed and incubated at 40° C. 0.1 ml of the enzyme solution is added and incubated for 1 hour. The reaction is terminated by adding 0.1 ml of 1 N HCl.

2 ml of $CHCl_3$-methanol (1:1) is added to the reaction mixture and mixed vigorously. Approx. 1 $\mu$(micro)l of the $CHCl_3$-methanol is taken and applied to a TLC rod (in triplicate or quadruplicate). the TLC rods are dried and developed for 45 minutes with $CHCl_3$: methanol: $NH_3$ (25% solution)=65:25:5. After the development, the rods are scanned by TLC-FID (Iatroscan), and the chromatograms are integrated.

The amounts of palmitate, the substrate, lysophosphatidyl choline (LPC) and glycerophosphatidyl choline (GPC) are calculated from the areas of peaks appearing in that order.

The result of the test is considered positive if GPC is formed without any LPC formation.

Amino Acid Sequence

Partial sequences SEQ ID NO: 1–8 were determined by sequencing of phospholipase from Hyphozyma sp. CBS 648.91 after enzymatic hydrolysis. In these sequences, Xaa represents an amino acid that could not be determined. SEQ ID NO: 1 is an N-terminal sequence, and the others are internal sequences. Xaa in SEQ ID NO: 1 is believed to be a Pro residue. Xaa in SEQ ID NO: 3, 7 and 8 and both Xaa in SEQ ID NO: 5 are believed to be glycosylated Asn residues.

A nearly complete DNA sequence (SEQ ID NO: 9) was determined for the gene encoding the phospholipase from Hyphozyma sp. CBS 648.91. This sequence was determined from the genomic locus and includes an open reading frame of 552 amino acids and 213 base pairs of sequence upstream of the putative translation initiation codon. The methods used for sequence isolation and determination are well known in the art. Details are given in the examples.

The long, uninterrupted open reading frame identified in this sequence was translated and compared to the partial peptide sequences SEQ ID NO: 1–8. The translated sequence was identical to seven of the partial peptide sequences at all positions, SEQ ID NO:1–7, and overlapped the most distal partial peptide sequence, SEQ ID NO: 8 by 10 amino acids. By combining the translation with partial peptide NO: 8, a sequence of 573 amino acid residues (shown as SEQ ID NO: 11) has been determined. The amino terminus of the mature peptide is determined by comparison with SEQ ID NO: 1. The sequenced open reading frame extends upstream an additional 115 amino acids. There is only one Met codon in this region, 76 amino acids from the start of the mature peptide (position −76). The 14 amino acids immediately following this methionine residue appear to constitute a secretion signal sequence (G. von Heijne, Nucleic Acids Res, 14, 4683–4690, 1986), indicating both that this is the translation initiation codon and that the encoded protein is secreted. The intervening 61 amino acids must constitute a propeptide.

The peptide sequence from Hyphozyma was aligned with the phospholipase B sequences from three other fungi, Penicillium notatum (Genbank X60348) (SEQ ID NO: 16) Saccharomyces cerevisiae (Genbank L23089) (SEQ ID NO: 17) and Torulaspora delbrueckii (Genbank D32134) (SEQ ID NO: 18) as shown in FIG. 4a–d. In this alignment a dash (-) indicates an inserted gap, a circle (o) above the alignment marks a position at which the same amino acid is found in all proteins, and a vertical line (l) above the alignment indicates similar residues in all proteins. The portion of the Hyphozyma phospholipase sequence we have determined is 38% identical to the phospholipase from Penicillium notatum, 37% identical to the phospholipase from Saccharomyces cerevisiae, and 38% identical to the phospholipase from Torulaspora delbrueckii. The full length Penicillium, Saccharomyces, and Torulaspora sequences extend from 112 to 145 residues further than the partial Hyphozyma sequence, suggesting that the full length for the translated Hyphozyma peptide is approximately 700 amino acid residues.

Thus, the phospholipase of the invention may contain an N-terminal sequence as shown at positions 1–497 of SEQ ID NO: 11 or a sequence derived therefrom by substitution, deletion or insertion of one or more amino acids. The derived sequence may be at least 50% identical, e.g. at least 60%, preferably at least 70%, especially at least 80 or at least 90% identical with said partial sequence. The phospholipase of the invention may contain a further 150–250 (e.g. 180–220) amino acid residues at the C-terminal.

Microorganism

The phospholipase of this invention may be derived from a fungal strain of the genus Hyphozyma, a genus of yeastlike Hyphomycetes described in de Hoog, G. S & Smith, M.Th., Antonie van Leeuwenhoek, 47, 339–352 (1981).

Preferably, the strain belongs to the species defined by the strain Hyphozyma sp. LF132, CBS 648.91, which is described in WO 93/24619. This strain was classified in the genus Hyphozyma, but it did not match any of the previously described species of Hyphozyma, so it is believed to define a new species. It is particularly preferred to use said strain or a mutant or variant thereof having the ability to produce phospholipase.

The preferred Hyphozyma sp. strain (designated LF132 by the inventors) has been deposited on 12 November 1991, for the purpose of patent procedures according to the Budapest Treaty at Centraal Bureau voor Schimmelcultures (CBS), Oosterstraat 1, 3740 AG Baarn, Netherlands, and was given the accession number CBS 648.91.

Production of Phospholipase by Cultivation of Hyphozyma

The phospholipase of the invention may be produced by cultivation of the microorganism described above in a suitable nutrient medium, containing carbon and nitrogen sources and inorganic salts, followed by recovery of the enzyme. The nutrient medium may be formulated according to principles well known in the art.

The phospholipase may be recovered from the culture broth and purified to remove lipase activity, e.g. as described in the examples of this specification.

Production by Cultivation of Transformant

An alternative method of producing the phospholipase of the invention comprises transforming a suitable host cell with a DNA sequence encoding the phospholipase, cultivating the transformed organism under conditions permitting the production of the enzyme, and recovering the enzyme from the culture.

The host organism is preferably a eukaryotic cell, in particular a fungal cell, such as a yeast cell or a filamentous fungal cell, preferably a strain of Aspergillus, Fusarium, Trichoderma or Saccharomyces, most preferably *A. niger, A. oryzae, F. graminearum, F. sambucinum, F. cerealis or S. cerevisiae*. The production of the phospholipase in such host organisms may be done by the general methods described in EP 238,023 (Novo Nordisk), WO 96/00787 (Novo Nordisk) or EP 244,234 (Alko).

The DNA sequence can be isolated from a phospholipase-producing Hyphozyma strain by extraction of DNA by methods known in the art, e.g. as described by Sambrook et al., (1989), Molecular Cloning: A Laboratory Manual. Cold Spring Harbor Lab.; Cold Spring Harbor, N.Y.

The DNA sequence of the invention can also be isolated by any general method involving cloning, in suitable vectors, a cDNA library from a phospholipase-producing Hyphozyma strain, transforming suitable yeast host cells with said vectors, culturing the host cells under suitable conditions to express any enzyme of interest encoded by a clone in the cDNA library, screening for positive clones by determining any phospholipase activity of the enzyme produced by such clones, and isolating the enzyme encoding DNA from such clones.

A general isolation method has been disclosed in WO 93/11249 or WO 94/14953, the contents of which are hereby incorporated by reference.

Alternatively, the DNA encoding a phospholipase of the invention may, in accordance with well-known procedures, conveniently be isolated from a phospholipase-producing Hyphozyma strain, by use of synthetic oligonucleotide probes prepared on the basis of a peptide sequence disclosed herein.

Use of phospholipase

The phospholipase of the invention can be used in any application where it is desired to hydrolyze the fatty acyl group(s) of a phospholipid or lyso-phospholipid, such as lecithin or lyso-lecithin. The phospholipase is preferably used at pH 1.5–5 (e.g. 3–5, particularly 3.5–4.5) and at 30–70° C. (particularly 40–60° C.). If desired, the phospholipase may be inactivated after the reaction by a heat treatment, e.g. at pH 7, 80° C. for 1 hour or 90° C. for 10 minutes.

As an example, the phospholipase of the invention can be used in the preparation of dough, bread and cakes, e.g. to improve the elasticity of the bread or cake. Thus, the phospholipase can be used in a process for making bread, comprising adding the phospholipase to the ingredients of a dough, kneading the dough and baking the dough to make the bread. This can be done in analogy with U.S. Pat. No. 4,567,046 (Kyowa Hakko), JP-A 60-78529 (QP Corp.), JP-A 62-111629 (QP Corp.), JP-A 63-258528 (QP Corp.) or EP 426211 (Unilever).

The phospholipase of the invention can also be used to improve the filterability of an aqueous solution or slurry of carbohydrate origin by treating it with the phospholipase. This is particularly applicable to a solution or slurry containing a starch hydrolysate, especially a wheat starch hydrolysate since this tends to be difficult to filter and to give cloudy filtrates. The treatment can be done in analogy with EP 219,269 (CPC International).

Treatment of Vegetable Oil

The phospholipase of the invention can be used in a process for reducing the content of phospholipid in an edible oil, comprising treating the oil with the phospholipase so as to hydrolyze a major part of the phospholipid, and separating an aqueous phase containing the hydrolyzed phospholipid from the oil. This process is applicable to the purification of any edible oil which contains phospholipid, e.g. vegetable oil such as soy bean oil, rape seed oil and sunflower oil.

Prior to the enzymatic treatment, the vegetable oil is preferably pretreated to remove slime (mucilage), e.g. by wet refining. Typically, the oil will contain 50–250 ppm of phosphorus as phospholipid at the start of the treatment with phospholipase, and the process of the invention can reduce this value to below 5–10 ppm.

The enzymatic treatment is conducted by dispersing an aqueous solution of the phospholipase, preferably as droplets with an average diameter below 10 $\mu$(micro)m. The amount of water is preferably 0.5–5% by weight in relation to the oil. An emulsifier may optionally be added. Mechanical agitation may be applied to maintain the emulsion.

The enzymatic treatment can be conducted at a pH in the range 1.5–5. The process pH may be in the range 3.5–5 in order to maximize the enzyme performance, or a pH in the range 1.5–3 (e.g. 2–3) may be used in order to suppress the alkaline hydrolysis of triglycerides (saponification). The pH may be adjusted by adding citric acid, a citrate buffer or HCl.

A suitable temperature is generally 30–70° C. (particularly 30–45° C., e.g. 35–40° C.). The reaction time will typically be 1–12 hours (e.g. 2–6 hours), and a suitable enzyme dosage will usually be 100–5000 IU per liter of oil (e.g. 200–2000 IU/l) or 0.1–10 mg/l (e.g. 0.5–5 mg/l).

The enzymatic treatment may be conducted batchwise, e.g. in a tank with stirring, or it may be continuous, e.g. a series of stirred tank reactors.

The enzymatic treatment is followed by separation of an aqueous phase and an oil phase. This separation may be performed by conventional means, e.g. centrifugation. The aqueous phase will contain phospholipase, and the enzyme may be re-used to improve the process economy.

In other respects, the process can be conducted according to principles known in the art, e.g. in analogy with U.S. Pat. No. 5,264,367 (Metallgesellschaft, Röhm); K. Dahlke & H. Buchold, INFORM, 6 (12), 1284–91 (1995); H. Buchold, Fat Sci. Technol., 95 (8), 300–304 (1993); JP-A 2–153997 (Showa Sangyo); or EP 654,527 (Metallgesellschaft, Röhm).

EXAMPLES

Example 1

Production of Phospholipase by Cultivation of Hyphozyma

The strain Hyphozyma sp. CBS 648.91, was cultivated in a nutrient medium containing the following components:

| | |
|---|---|
| Glucose | 20 g/l |
| Peptone | 10 g/l |
| MgSO$_4$, 7H$_2$O | 1 g/l |
| Yeast Extract | 10 g/l |
| K$_2$HPO$_4$ | 5 g/l | pH adjusted to 6.5 with NaOH

The strain was cultivated at 27–30° C. for 3–4 days. The culture broth was subjected to liquid/solid separation by centrifugation. After centrifugation, a phospholipase activity of 1 unit/g culture broth was obtained (unit defined above). The supernatant was desalted and freeze-dried resulting in a crude powder preparation.

Example 2

Purification of Phospholipase

Freeze dried phospholipase powder obtained according to Example 1 (300 units/g) was applied on a Butyl Toyopearl 650M column after adjusting the salt concentration to 3.5 M ammonium acetate. Bound phospholipase activity was eluted with H$_2$O and separated from lipase activity which was also present in the crude powder preparation.

Fractions containing phospholipase activity were pooled, concentrated and dialyzed. The concentrated preparation was treated by anion exchange column chromatography using DEAE Toyopearl 650M. The adsorption condition was pH 7.5 (50 mM Tris-HCl) and elution was carried out by a linear gradient of 0–0.5M NaCl.

The last step was gel filtration column chromatography using HiLoad 26/60 Superdex 200 pg. The condition was 50 mM Tris-HCl pH 7.5 including 0.5M NaCl. The resulting purified phospholipase was used in the following examples.

Example 3

Characterization of Phospholipase

The molecular weight (MW) of the phospholipase was found to be about 94 kDa on SDS PAGE and 87 kDa by gel filtration column chromatography. The polypeptide is believed to be glycosylated. The pI is around 5.6 on IEF PAGE.

The temperature profile was determined at pH 3.0 and 4.0 in a range of 40 to 70° C. The phospholipase was incubated for 10 minutes, and the activity was determined by the method described above. The temperature profile is presented in FIG. 1 as relative activity (taking the maximum activity as 100%). It is seen from this figure that both at pH 3 and 4, the phospholipase has high activity (more than 50% of optimum) at temperatures of 40 to 60° C. with a temperature optimum around 50° C.

The pH profile was determined at 40° C. using glycine-HCl buffer at pH 2, 2,5 and 3, and citrate buffer at pH 3, 4, 5 and 6. The results are presented in FIG. 2 as relative activity (taking the maximum activity as 100%). Due to a change of buffer system (glycine-HCl, citrate), the figure is made up of two curves, one representing the interval of pH 2.0 to 3.0 and the other representing the interval of pH 3.0 to 6.0. From the figure it appears that the phospholipase is active at pH values of 2 to 5, and the pH optimum is around 3.

The thermostability was determined by incubating in 0.1 M phosphate buffer (pH 7) for 10 minutes at temperatures of 40–80° C. and determining the residual activity after the incubation. The results were 100% at 40° C., 95% at 50° C., 82% at 60° C., 55% at 70° C. and 9% at 80° C. These results are also shown in FIG. 3.

Example 4

Hydrolysis of Phospholipid

A substrate solution was prepared by dissolving 2% of crude soy bean lecithin (phosphatidyl choline) in water. An enzyme solution was prepared by 50 times dilution of the purified enzyme from Example 2. 0.5 ml of the substrate solution, 0.25 ml of 0.4 M citrate buffer (pH 4) and 0.05 ml of 0.1 N CaCl$_2$ were mixed and incubated at 60° C. 0.1 ml of the enzyme solution was added and incubated for 1 hour at 60° C. The reaction was terminated by adding 0.1 ml of 1 N HCl. The mixture after the reaction was analyzed by TLC-latroscan as described above in the assay for reaction pattern.

The results showed that fatty acid was formed and that no lecithin remained after the reaction. A solid precipitate was observed at the bottom of the reaction vessel. This was believed to be a mixture of phospholipid and fatty acid.

Example 5

Hydrolysis of Lyso-phospholipid

Lyso-phosphatidylcholine (LPC) was treated for 10 minutes at 40° C., other conditions being the same as described in Example 4. The chromatogram showed that about two thirds of the LPC was hydrolyzed, and that fatty acid was formed together with a small amount of phosphatidylcholine.

Example 6

Enzymatic Degumming of Edible Oil

Vegetable oil was degummed by treating it with phospholipase from Hyphozyma as follows. The enzyme dosage, the reaction pH and temperature were varied, and the resulting content of phospholipid was measured.

The equipment consisted of a 1 l jacketed steel reactor fitted with a steel lid, a propeller (600 rpm), baffles, a temperature sensor, an inlet tube at the top, a reflux condenser (4° C.) at the top, and an outlet tube at the bottom. The reactor jacket was connected to a thermostat bath. The outlet tube was connected via silicone tubing to an in-line mixer head equipped with a high shear screen (8500 rpm, flow ca. 1.1 l/minute).The mixer head was fitted with a cooling coil (5–10° C.) and an outlet tube, which was connected to the inlet tube of the reactor via silicone tubing. A temperature sensor was inserted in the silicone tubing just after the mixer head. The only connection from the reactor/mixer head system to the atmosphere was through the reflux condenser.

In each experiment, 0.6 l (ca. 560 g) of water-degummed rape seed oil with a P content of 186–252 ppm was loaded into the reactor with the thermostat and lab mixer running and pre-treated for 30 minutes with 0.6 g (2.86 mmol) of citric acid monohydrate in 27 g of water (added water vs. oil equals 4.8% w/w; [citric acid] in water phase=106 mM, in water/oil emulsion=4.6 mM) at time=0. After the pre-treatment, the pH was adjusted by adding a NaOH solution followed by the enzyme solution. The mixture was then incubated for 6 hours, and samples for P-analysis and pH determination were drawn at intervals throughout the experiment.

The determination of phosphorous content in the oil was done according to procedure 2.421 in "Standard Methods for the Analysis of Oils, Fats, and Derivatives, 7.th ed. (1987)" after separating the emulsion by heating and centrifugation.

The initial performance was calculated from the initial rate of phosphorus removal from the oil, taking the optimum as 100%.

Degumming at Various pH

The oil was treated at 40° C. with an enzyme dosage of 1.3 mg/kg oil (as pure enzyme protein). The results at various pH were as follows:

| pH | Initial performance (relative to optimum) | P content after 6 hours |
| --- | --- | --- |
| 3.0 | 40 | 74 ppm |
| 3.7 | 90 | <10 ppm |
| 4.4 | 100 | <10 ppm |
| 4.8 | 80 | <10 ppm |

Degumming at Varioustemperatures

The oil was treated at pH 4.5 with an enzyme dosage of 1.3 mg/kg oil (as pure enzyme protein). The results at various temperatures were as follows:

| Temperature | Initial performance (relative to optimum) | P content after 6 hours |
| --- | --- | --- |
| 35° C. | 90 | <10 ppm |
| 40° C. | 100 | <10 ppm |

Degumming with Various Enzyme Dosages

The oil was treated at pH 4.5, 40° C. The results at various enzyme dosages (given as pure enzyme protein) were as follows:

| Enzyme dosage | Initial performance (relative to optimum) | P content after 6 hours |
| --- | --- | --- |
| 0.65 mg/kg oil | 70 | <10 ppm |
| 1.3 | 100 | <10 ppm |
| 2.6 | 100 | <10 ppm |

The results show good degumming performance at pH 3.5–5, 35–40° C. Good degumming to a phosphorus content below 10 ppm was obtained in 6 hours with a dosage of 1.3 mg/kg oil, and in 3 hours at a dosage of 2.6 mg/kg.

Measurement of the free fatty acids generated during degumming showed a low level of free fatty acids, corresponding very well to the amount of phospholipid in the substrate oil.

For reference, similar experiments were done with prior-art phospholipase from porcine pancreas. It was found that degumming to below 10 ppm of phosphorus could be obtained at 60° C., pH 5.5, but the performance of the prior-art enzyme dropped sharply at lower pH, and satisfactory degumming could not be achieved at pH lower than 5.5.

Example 7

Partial Determination of the DNA Sequence Encoding the Phospholipase

DNA encoding the phospholipase of Hyphozyma was isolated by two different methods. The 5' end of the gene was isolated by cloning. A genomic library of Hyphozyma DNA partially digested with Sau3A was screened at high stringency using standard methods (Sambrook et al., (1989), Molecular Cloning: A Laboratory Manual. Cold Spring Harbor Lab.; Cold Spring Harbor, N.Y.) with a probe specific to the phospholipase sequence. This probe was amplified from total Hyphozyma DNA with degenerate primers designed using the previously determined partial peptide sequences with SEQ ID NO: 1 and 5. Standard PCR conditions were used for amplification (Saiki el al., Science, 239, 487–491, 1988), including 0.5 mM $MgCl_2$, a 45° C. annealing temperature, and primers PLMStr1 (SEQ ID NO: 12) and PLMStr6 (SEQ ID NO: 13). The clone pMStr16 hybridized to the probe, and therefore was isolated and a portion of the insert was sequenced.

An additional internal portion of the phospholipase-encoding gene was isolated using PCR with Hyphozyma DNA and the primers PLHaW2 (SEQ ID NO: 14) and PLMStr7 (SEQ ID NO: 15). PLHaW2 was designed using the sequence determined from pMStr16, and PLMStr7 was designed from the sequence of the partial peptide with SEQ ID NO: 8. Standard conditions were used for the PCR reactions, with 1.5 mM $MgCl_2$, and a 46° C. annealing temperature. The resulting amplified fragment was isolated and sequenced.

What is claimed is:

1. An isolated phospholipase enzyme derived from Hyphozyma which hydrolyzes both fatty acyl groups in a phospholipid and is essentially free of lipase activity, wherein the phospholipase enzyme has a temperature optimum at about 50° C., measured at pH 3–4 for 10 minutes, and a pH optimum of about pH 3, measured at 40° C. for 10 minutes.

2. The phospholipase of claim 1 derived from Hyphozyma sp. strain CBS 648.91.

3. An isolated phospholipase enzyme which hydrolyes both acyl groups in a phospholipid and is essentially free of lipase activity comprising one of:
   (a) an N-terminal amino acid sequence having the sequence shown in positions 1–497 of SEQ ID NO: 11; or
   (b) a polypeptide comprising at least 90% identity to the amino acid sequence of SEQ ID NO: 11.

4. The phospholipase of claim 3 derived from Hyphozyma sp. strain CBS 648.91.

5. A process for hydrolyzing fatty acyl groups in a phospholipid or lysophospholipid, comprising treating the phospholipid or lysophospholipid with the phospholipase of claim 1.

6. The process of claim 5 wherein the phospholipid or lysophospholipid comprises lecithin or lysolecithin.

7. The process of claim 5 wherein the treatment is conducted at pH 1.5–5 and 30–70° C.

8. The process of claim 5, which is a process for improving the filterability of an aqueous solution or slurry of carbohydrate origin which contains phospholipid.

9. The process of claim 8 wherein the solution or slurry contains a starch hydrolysate.

10. The process of claim 5 which is a process for making bread, comprising adding the phospholipase to the ingredients of a dough, kneading the dough and baking the dough to make the bread.

11. The process of claim 5 which is a process for reducing the content of phospholipid in an edible oil, comprising treating the oil with the phospholipase so as to hydrolyze a major part of the phospholipid, and separating an aqueous phase containing the hydrolyzed phospholipid from the oil.

12. A process for removing phospholipid from an edible oil, comprising:
   a) treating the oil at pH 1.5–3 with a dispersion of an aqueous solution of the phospholipase of claim 1, and
   b) separating an aqueous phase containing the hydrolyzed phospholipid from the oil.

13. The method of claim 12 wherein the oil is treated to remove mucilage prior to the treatment with the phospholipase.

14. The method of claim 12 wherein the oil prior to the treatment with the phospholipase contains the phospholipid in an amount corresponding to 50–250 ppm of phosphorus.

15. The process of claim 12 wherein the treatment with phospholipase is done at 30–45° C. for 1–12 hours at a phospholipase dosage of 0.1–10 mg/l in the presence of 0.5–5% of water.

* * * * *

SEQUENCE LISTING

<160> NUMBER OF SEQ ID NOS: 18

<210> SEQ ID NO 1
<211> LENGTH: 16
<212> TYPE: PRT
<213> ORGANISM: Hyphozyma sp. CBS 648.91
<220> FEATURE:
<223> OTHER INFORMATION: Xaa at position 15 is any amino acid

<400> SEQUENCE: 1

Ala Ser Pro Ser Gly Ser Tyr Ala Pro Ala Asn Met Pro Cys Xaa Gln
 1               5                  10                  15

<210> SEQ ID NO 2
<211> LENGTH: 7
<212> TYPE: PRT
<213> ORGANISM: Hyphozyma sp. CBS 648.91

<400> SEQUENCE: 2

Asp Trp Ala Lys Trp Leu Ser
 1               5

<210> SEQ ID NO 3
<211> LENGTH: 28
<212> TYPE: PRT
<213> ORGANISM: Hyphozyma sp. CBS 648.91
<220> FEATURE:
<223> OTHER INFORMATION: Xaa at position 4 is any amino acid

<400> SEQUENCE: 3

Asp Gly Arg Xaa Glu Thr Ala Asn Gln Arg Gly Thr Gly Gly Leu Leu
 1               5                  10                  15

Gln Leu Ala Glu Tyr Ile Ala Gly Leu Ser Gly Gly
            20                  25

<210> SEQ ID NO 4
<211> LENGTH: 36
<212> TYPE: PRT
<213> ORGANISM: Hyphozyma sp. CBS 648.91

<400> SEQUENCE: 4

Asp Leu Glu Ser Asn Leu Ile Val Pro Glu Asp Gly Lys Val Ser Phe
 1               5                  10                  15

Tyr Ala Ser Ile Leu Ala Ala Val Ala Gly Lys Arg Asn Glu Gly Tyr
            20                  25                  30

Gln Thr Ser Leu
        35

<210> SEQ ID NO 5
<211> LENGTH: 41
<212> TYPE: PRT
<213> ORGANISM: Hyphozyma sp. CBS 648.91
<220> FEATURE:
<223> OTHER INFORMATION: Xaa at position 13 and 30 is any amino acid

<400> SEQUENCE: 5

Asp Glu Arg Glu Pro Gly Glu Leu Ile Ile Pro Arg Xaa Thr Thr Ile
 1               5                  10                  15

Trp Glu Phe Asn Pro Tyr Glu Phe Gly Ser Trp Asn Pro Xaa Val Ser
            20                  25                  30

Ala Phe Ile Pro Ile Glu Ile Leu Gly
        35                  40

```
<210> SEQ ID NO 6
<211> LENGTH: 15
<212> TYPE: PRT
<213> ORGANISM: Hyphozyma sp. CBS 648.91

<400> SEQUENCE: 6

Asp Val Ser Leu Val Pro Asn Pro Phe Tyr Gly Tyr Val Gly Glu
 1               5                  10                  15

<210> SEQ ID NO 7
<211> LENGTH: 30
<212> TYPE: PRT
<213> ORGANISM: Hyphozyma sp. CBS 648.91
<220> FEATURE:
<223> OTHER INFORMATION: Xaa at position 7 is any amino acid

<400> SEQUENCE: 7

Asp Val Thr Asn Trp Pro Xaa Ala Ser Ala Leu Tyr Gln Thr Ser Leu
 1               5                  10                  15

Arg Ala Gln Tyr Pro Thr Tyr Ser Gln Tyr Ala Phe Pro Val
            20                  25                  30

<210> SEQ ID NO 8
<211> LENGTH: 31
<212> TYPE: PRT
<213> ORGANISM: Hyphozyma sp. CBS 648.91
<220> FEATURE:
<223> OTHER INFORMATION: Xaa at position 5 is any amino acid

<400> SEQUENCE: 8

Asp Thr Ser Phe Xaa Gly Thr Lys Thr Pro Ile Ile Val Tyr Met Pro
 1               5                  10                  15

Ser Tyr Pro Tyr Ala Ala Phe Ala Asp Thr Ser Thr Phe Lys Leu
            20                  25                  30

<210> SEQ ID NO 9
<211> LENGTH: 1870
<212> TYPE: DNA (genomic)
<213> ORGANISM: Hyphozyma sp. CBS 648.91
<220> FEATURE:
<221> NAME/KEY: CDS
<222> LOCATION: (214)...(1869)
<221> NAME/KEY: mat_peptide
<222> LOCATION: (442)...(1869)

<400> SEQUENCE: 9
ggcgagtgca caaggccgcg gaccaaatgt ccctgagtgc gtgtgtttgt gtgtgacata      60
gccagcagaa tgcagcttac tcttcttcca ttgtgagacg ttatataccc acacacatct    120
cgccgtcccg tcagacccctt ctgcatccgt ccgtacgaac ctgctctctt ccatttacct   180
cgacactgta tcgagtgcac gcttcgaggc atc atg aag ctg ccg ctc ctc tct     234
                                    Met Lys Leu Pro Leu Leu Ser
                                     1               5 acg ctg ctc agc ctc gcg ctg acc gcc tcg acc gtc gtc cgt gcc tat     282
Thr Leu Leu Ser Leu Ala Leu Thr Ala Ser Thr Val Val Arg Ala Tyr
        10                  15                  20 ccc tcc atc ccg gcg cag ctc acc gaa gac gag atc acc cgc atc agc     330
Pro Ser Ile Pro Ala Gln Leu Thr Glu Asp Glu Ile Thr Arg Ile Ser
    25                  30                  35 cag ctc tcc cag gag gac aag gtc aag ttt gcc gaa cgc atc cta gag     378
Gln Leu Ser Gln Glu Asp Lys Val Lys Phe Ala Glu Arg Ile Leu Glu
 40                  45                  50                  55
```

```
att cgc acc gcc tac gag tat gag aag cag cag cta gcc cgt caa cat      426
Ile Arg Thr Ala Tyr Glu Tyr Glu Lys Gln Gln Leu Ala Arg Gln His
             60                  65                  70 gcg ctc gag cga cgc gcc tcg ccc tcg ggc tcg tac gca cct gcc aac      474
Ala Leu Glu Arg Arg Ala Ser Pro Ser Gly Ser Tyr Ala Pro Ala Asn
         75                  80                  85 atg ccc tgc ccc cag cga acg tcc cag cag ggt ccc ggc ttc atc cga      522
Met Pro Cys Pro Gln Arg Thr Ser Gln Gln Gly Pro Gly Phe Ile Arg
         90                  95                 100 ccc gcc aag acc aag cag ctc tca atc tcg gaa gcc gac tat gtc tcg      570
Pro Ala Lys Thr Lys Gln Leu Ser Ile Ser Glu Ala Asp Tyr Val Ser
    105                 110                 115 cgc cgc cgc acc aac acc cag gcc gac tgg gcc aag tgg ctc tcg gac      618
Arg Arg Arg Thr Asn Thr Gln Ala Asp Trp Ala Lys Trp Leu Ser Asp
120                 125                 130                 135 tcg gcc aag ctc aac agc agc ctg ccc ggc ggt gcc tcc aac tac acc      666
Ser Ala Lys Leu Asn Ser Ser Leu Pro Gly Gly Ala Ser Asn Tyr Thr
                140                 145                 150 tcg tcg acc gac cgc gtg cct cgt ctg ggc ttt gcg ctc agc ggc ggt      714
Ser Ser Thr Asp Arg Val Pro Arg Leu Gly Phe Ala Leu Ser Gly Gly
            155                 160                 165 gga ctg cgt gcc atg ctc gtt ggt tcg ggc acg ctc cag ggc ttt gac      762
Gly Leu Arg Ala Met Leu Val Gly Ser Gly Thr Leu Gln Gly Phe Asp
        170                 175                 180 ggc cgc aac gag acc gcc aac cag cgt ggc acc ggt gga ctg ctc cag      810
Gly Arg Asn Glu Thr Ala Asn Gln Arg Gly Thr Gly Gly Leu Leu Gln
185                 190                 195 ctt gcc gag tac att gcc ggc ctg tcc ggc ggc tcg tgg gcg acc gcc      858
Leu Ala Glu Tyr Ile Ala Gly Leu Ser Gly Gly Ser Trp Ala Thr Ala
200                 205                 210                 215 agt ctc acc atg aac aac tgg gcc acc acc cag tcg ctc aag gac aac      906
Ser Leu Thr Met Asn Asn Trp Ala Thr Thr Gln Ser Leu Lys Asp Asn
                220                 225                 230 atc tgg gat ctc gag tcc aac ctc atc gtc ccc gag gac ggc aag gtc      954
Ile Trp Asp Leu Glu Ser Asn Leu Ile Val Pro Glu Asp Gly Lys Val
            235                 240                 245 tcg ttt tac gcc tcg atc ctg gcc gcc gtc gcg ggc aag agg aac gaa     1002
Ser Phe Tyr Ala Ser Ile Leu Ala Ala Val Ala Gly Lys Arg Asn Glu
        250                 255                 260 ggt tac cag acc agt ctc acc gac tac ttt ggc ctc tcg atc gcc gac     1050
Gly Tyr Gln Thr Ser Leu Thr Asp Tyr Phe Gly Leu Ser Ile Ala Asp
265                 270                 275 aag att ctc aac ggc tcc atg tac ggc aac aag ttc agc gtc gag tgg     1098
Lys Ile Leu Asn Gly Ser Met Tyr Gly Asn Lys Phe Ser Val Glu Trp
280                 285                 290                 295 agc gac gtc aag aat acg tcc aag ttc acc gat gcc tcc atg ccg ttc     1146
Ser Asp Val Lys Asn Thr Ser Lys Phe Thr Asp Ala Ser Met Pro Phe
                300                 305                 310 ccc atc att att gcc gac gag cgc gag ccc ggc gag ctc atc atc ccg     1194
Pro Ile Ile Ile Ala Asp Glu Arg Glu Pro Gly Glu Leu Ile Ile Pro
            315                 320                 325 cgc aac acc acc atc tgg gag ttc aac ccg tac gag ttc ggt tct tgg     1242
Arg Asn Thr Thr Ile Trp Glu Phe Asn Pro Tyr Glu Phe Gly Ser Trp
        330                 335                 340 aac ccc aat gtt tcg gct ttc atc ccc atc gag atc ctc ggc tcg agt     1290
Asn Pro Asn Val Ser Ala Phe Ile Pro Ile Glu Ile Leu Gly Ser Ser
345                 350                 355 ctg gac aac ggc acc agc gtc ctg ccc gac ggc gtc tgt gtc ggc gga     1338
Leu Asp Asn Gly Thr Ser Val Leu Pro Asp Gly Val Cys Val Gly Gly
360                 365                 370                 375
```

```
tac gag acc gtt gcc tgg gtg act ggc acc tcg gcg act ctg ttc tct    1386
Tyr Glu Thr Val Ala Trp Val Thr Gly Thr Ser Ala Thr Leu Phe Ser
                380                 385                 390 ggt ctg tac ctc gaa ctt atc tcg acc tcg agc aac aac atc atc gtc    1434
Gly Leu Tyr Leu Glu Leu Ile Ser Thr Ser Ser Asn Asn Ile Ile Val
            395                 400                 405 gat gcg ctc aag gag att gcc cag gcg gta tca aac gag cag aac gat    1482
Asp Ala Leu Lys Glu Ile Ala Gln Ala Val Ser Asn Glu Gln Asn Asp
        410                 415                 420 gtc tcg ctc gtg ccc aac ccg ttc tac ggc tac gtc ggc gaa ggc gac    1530
Val Ser Leu Val Pro Asn Pro Phe Tyr Gly Tyr Val Gly Glu Gly Asp
    425                 430                 435 gtc caa gtg tcg gac ctg cgc aat att acg ctc gtc gat ggt ggt ctc    1578
Val Gln Val Ser Asp Leu Arg Asn Ile Thr Leu Val Asp Gly Gly Leu
440                 445                 450                 455 gac aac gag aat gtg cca ctc tgg ccg ctt gtc gag ccg gcg cgc gat    1626
Asp Asn Glu Asn Val Pro Leu Trp Pro Leu Val Glu Pro Ala Arg Asp
                460                 465                 470 ctg gac gtg atc atc gcc att gac agc tcg gcg gac gtg acc aac tgg    1674
Leu Asp Val Ile Ile Ala Ile Asp Ser Ser Ala Asp Val Thr Asn Trp
            475                 480                 485 ccg aac gcg tcg gcg ctg tac cag acg tcg ctg cgt gct cag tac ccg    1722
Pro Asn Ala Ser Ala Leu Tyr Gln Thr Ser Leu Arg Ala Gln Tyr Pro
        490                 495                 500 acc tat agc cag tac gcg ttc ccg gtg atg ccg gac acc aac acg gtg    1770
Thr Tyr Ser Gln Tyr Ala Phe Pro Val Met Pro Asp Thr Asn Thr Val
    505                 510                 515 gtc aac cgc ggc ctc aac acg cgc ccc gtg ttc tac ggc tgc aat gcg    1818
Val Asn Arg Gly Leu Asn Thr Arg Pro Val Phe Tyr Gly Cys Asn Ala
520                 525                 530                 535 acc gtc aac gtc acc aac gcg gat acg tcg ttc aac ggc acc aag acg    1866
Thr Val Asn Val Thr Asn Ala Asp Thr Ser Phe Asn Gly Thr Lys Thr
                540                 545                 550 cca a                                                              1870
Pro

<210> SEQ ID NO 10
<211> LENGTH: 552
<212> TYPE: PRT
<213> ORGANISM: Hyphozyma sp. CBS 648.91

<400> SEQUENCE: 10

Met Lys Leu Pro Leu Leu Ser Thr Leu Leu Ser Leu Ala Leu Thr Ala
1               5                   10                  15

Ser Thr Val Val Arg Ala Tyr Pro Ser Ile Pro Ala Gln Leu Thr Glu
            20                  25                  30

Asp Glu Ile Thr Arg Ile Ser Gln Leu Ser Gln Glu Asp Lys Val Lys
        35                  40                  45

Phe Ala Glu Arg Ile Leu Glu Ile Arg Thr Ala Tyr Glu Tyr Glu Lys
    50                  55                  60

Gln Gln Leu Ala Arg Gln His Ala Leu Glu Arg Ala Ser Pro Ser
65                  70                  75                  80

Gly Ser Tyr Ala Pro Ala Asn Met Pro Cys Pro Gln Arg Thr Ser Gln
                85                  90                  95

Gln Gly Pro Gly Phe Ile Arg Pro Ala Lys Thr Lys Gln Leu Ser Ile
            100                 105                 110

Ser Glu Ala Asp Tyr Val Ser Arg Arg Thr Asn Thr Gln Ala Asp
        115                 120                 125
```

```
Trp Ala Lys Trp Leu Ser Asp Ser Ala Lys Leu Asn Ser Ser Leu Pro
    130                 135                 140

Gly Gly Ala Ser Asn Tyr Thr Ser Ser Thr Asp Arg Val Pro Arg Leu
145                 150                 155                 160

Gly Phe Ala Leu Ser Gly Gly Leu Arg Ala Met Leu Val Gly Ser
                165                 170                 175

Gly Thr Leu Gln Gly Phe Asp Gly Arg Asn Glu Thr Ala Asn Gln Arg
                180                 185                 190

Gly Thr Gly Gly Leu Leu Gln Leu Ala Glu Tyr Ile Ala Gly Leu Ser
            195                 200                 205

Gly Gly Ser Trp Ala Thr Ala Ser Leu Thr Met Asn Asn Trp Ala Thr
210                 215                 220

Thr Gln Ser Leu Lys Asp Asn Ile Trp Asp Leu Glu Ser Asn Leu Ile
225                 230                 235                 240

Val Pro Glu Asp Gly Lys Val Ser Phe Tyr Ala Ser Ile Leu Ala Ala
                245                 250                 255

Val Ala Gly Lys Arg Asn Glu Gly Tyr Gln Thr Ser Leu Thr Asp Tyr
                260                 265                 270

Phe Gly Leu Ser Ile Ala Asp Lys Ile Leu Asn Gly Ser Met Tyr Gly
                275                 280                 285

Asn Lys Phe Ser Val Glu Trp Ser Asp Val Lys Asn Thr Ser Lys Phe
290                 295                 300

Thr Asp Ala Ser Met Pro Phe Pro Ile Ile Ile Ala Asp Glu Arg Glu
305                 310                 315                 320

Pro Gly Glu Leu Ile Ile Pro Arg Asn Thr Thr Ile Trp Glu Phe Asn
                325                 330                 335

Pro Tyr Glu Phe Gly Ser Trp Asn Pro Asn Val Ser Ala Phe Ile Pro
                340                 345                 350

Ile Glu Ile Leu Gly Ser Ser Leu Asp Asn Gly Thr Ser Val Leu Pro
                355                 360                 365

Asp Gly Val Cys Val Gly Gly Tyr Glu Thr Val Ala Trp Val Thr Gly
                370                 375                 380

Thr Ser Ala Thr Leu Phe Ser Gly Leu Tyr Leu Glu Leu Ile Ser Thr
385                 390                 395                 400

Ser Ser Asn Asn Ile Ile Val Asp Ala Leu Lys Glu Ile Ala Gln Ala
                405                 410                 415

Val Ser Asn Glu Gln Asn Asp Val Ser Leu Val Pro Asn Pro Phe Tyr
                420                 425                 430

Gly Tyr Val Gly Glu Gly Asp Val Gln Val Ser Asp Leu Arg Asn Ile
                435                 440                 445

Thr Leu Val Asp Gly Gly Leu Asp Asn Glu Asn Val Pro Leu Trp Pro
            450                 455                 460

Leu Val Glu Pro Ala Arg Asp Leu Asp Val Ile Ala Ile Asp Ser
465                 470                 475                 480

Ser Ala Asp Val Thr Asn Trp Pro Asn Ala Ser Ala Leu Tyr Gln Thr
                485                 490                 495

Ser Leu Arg Ala Gln Tyr Pro Thr Tyr Ser Gln Tyr Ala Phe Pro Val
                500                 505                 510

Met Pro Asp Thr Asn Thr Val Val Asn Arg Gly Leu Asn Thr Arg Pro
            515                 520                 525

Val Phe Tyr Gly Cys Asn Ala Thr Val Asn Val Thr Asn Ala Asp Thr
            530                 535                 540
```

```
Ser Phe Asn Gly Thr Lys Thr Pro
545                 550

<210> SEQ ID NO 11
<211> LENGTH: 573
<212> TYPE: PRT
<213> ORGANISM: Hyphozyma sp.  CBS 648.91

<400> SEQUENCE: 11

Met Lys Leu Pro Leu Leu Ser Thr Leu Leu Ser Leu Ala Leu Thr Ala
1               5                   10                  15

Ser Thr Val Val Arg Ala Tyr Pro Ser Ile Pro Ala Gln Leu Thr Glu
            20                  25                  30

Asp Glu Ile Thr Arg Ile Ser Gln Leu Ser Gln Glu Asp Lys Val Lys
        35                  40                  45

Phe Ala Glu Arg Ile Leu Glu Ile Arg Thr Ala Tyr Glu Tyr Glu Lys
50                  55                  60

Gln Gln Leu Ala Arg Gln His Ala Leu Glu Arg Arg Ala Ser Pro Ser
65                  70                  75                  80

Gly Ser Tyr Ala Pro Ala Asn Met Pro Cys Pro Gln Arg Thr Ser Gln
                85                  90                  95

Gln Gly Pro Gly Phe Ile Arg Pro Ala Lys Thr Lys Gln Leu Ser Ile
            100                 105                 110

Ser Glu Ala Asp Tyr Val Ser Arg Arg Arg Thr Asn Thr Gln Ala Asp
        115                 120                 125

Trp Ala Lys Trp Leu Ser Asp Ser Ala Lys Leu Asn Ser Ser Leu Pro
130                 135                 140

Gly Gly Ala Ser Asn Tyr Thr Ser Thr Asp Arg Val Pro Arg Leu
145                 150                 155                 160

Gly Phe Ala Leu Ser Gly Gly Leu Arg Ala Met Leu Val Gly Ser
                165                 170                 175

Gly Thr Leu Gln Gly Phe Asp Gly Arg Asn Glu Thr Ala Asn Gln Arg
            180                 185                 190

Gly Thr Gly Gly Leu Leu Gln Leu Ala Glu Tyr Ile Ala Gly Leu Ser
        195                 200                 205

Gly Gly Ser Trp Ala Thr Ala Ser Leu Thr Met Asn Asn Trp Ala Thr
210                 215                 220

Thr Gln Ser Leu Lys Asp Asn Ile Trp Asp Leu Glu Ser Asn Leu Ile
225                 230                 235                 240

Val Pro Glu Asp Gly Lys Val Ser Phe Tyr Ala Ser Ile Leu Ala Ala
                245                 250                 255

Val Ala Gly Lys Arg Asn Glu Gly Tyr Gln Thr Ser Leu Thr Asp Tyr
            260                 265                 270

Phe Gly Leu Ser Ile Ala Asp Lys Ile Leu Asn Gly Ser Met Tyr Gly
        275                 280                 285

Asn Lys Phe Ser Val Glu Trp Ser Asp Val Lys Asn Thr Ser Lys Phe
290                 295                 300

Thr Asp Ala Ser Met Pro Phe Pro Ile Ile Ile Ala Asp Glu Arg Glu
305                 310                 315                 320

Pro Gly Glu Leu Ile Ile Pro Arg Asn Thr Thr Ile Trp Glu Phe Asn
                325                 330                 335

Pro Tyr Glu Phe Gly Ser Trp Asn Pro Asn Val Ser Ala Phe Ile Pro
            340                 345                 350

Ile Glu Ile Leu Gly Ser Ser Leu Asp Asn Gly Thr Ser Val Leu Pro
        355                 360                 365
```

```
Asp Gly Val Cys Val Gly Tyr Glu Thr Val Ala Trp Val Thr Gly
    370                 375                 380

Thr Ser Ala Thr Leu Phe Ser Gly Leu Tyr Leu Glu Leu Ile Ser Thr
385                 390                 395                 400

Ser Ser Asn Asn Ile Ile Val Asp Ala Leu Lys Glu Ile Ala Gln Ala
                405                 410                 415

Val Ser Asn Glu Gln Asn Asp Val Ser Leu Val Pro Asn Pro Phe Tyr
            420                 425                 430

Gly Tyr Val Gly Glu Gly Asp Val Gln Val Ser Asp Leu Arg Asn Ile
        435                 440                 445

Thr Leu Val Asp Gly Gly Leu Asp Asn Glu Asn Val Pro Leu Trp Pro
    450                 455                 460

Leu Val Glu Pro Ala Arg Asp Leu Asp Val Ile Ile Ala Ile Asp Ser
465                 470                 475                 480

Ser Ala Asp Val Thr Asn Trp Pro Asn Ala Ser Ala Leu Tyr Gln Thr
                485                 490                 495

Ser Leu Arg Ala Gln Tyr Pro Thr Tyr Ser Gln Tyr Ala Phe Pro Val
            500                 505                 510

Met Pro Asp Thr Asn Thr Val Val Asn Arg Gly Leu Asn Thr Arg Pro
        515                 520                 525

Val Phe Tyr Gly Cys Asn Ala Thr Val Asn Val Thr Asn Ala Asp Thr
    530                 535                 540

Ser Phe Asn Gly Thr Lys Thr Pro Ile Ile Val Tyr Met Pro Ser Tyr
545                 550                 555                 560

Pro Tyr Ala Ala Phe Ala Asp Thr Ser Thr Phe Lys Leu
                565                 570

<210> SEQ ID NO 12
<211> LENGTH: 20
<212> TYPE: DNA
<213> ORGANISM: Primer
<220> FEATURE:
<221> NAME/KEY:
<222> LOCATION:
<223> OTHER INFORMATION: n at position 3,6,9,18 is deoxyinosine

<400> SEQUENCE: 12
gcnccngcna ayatgccntg                                              20

<210> SEQ ID NO 13
<211> LENGTH: 20
<212> TYPE: DNA
<213> ORGANISM: Primer
<220> FEATURE:
<221> NAME/KEY:
<222> LOCATION:
<223> OTHER INFORMATION: n at position 6 is deoxyinosine

<400> SEQUENCE: 13
tcgtangggt traaytccca                                              20

<210> SEQ ID NO 14
<211> LENGTH: 17
<212> TYPE: DNA
<213> ORGANISM: Primer

<400> SEQUENCE: 14
ccatgctcgt tggttcg                                                 17
```

```
<210> SEQ ID NO 15
<211> LENGTH: 17
<212> TYPE: DNA
<213> ORGANISM: Primer

<400> SEQUENCE: 15
ggcatgtaga cgatgat                                                  17

<210> SEQ ID NO 16
<211> LENGTH: 612
<212> TYPE: PRT
<213> ORGANISM: Penicillium notatum

<400> SEQUENCE: 16
```

Asp Ile Thr Phe Ala Gly Val Gln Arg Ala Leu Pro Asn Ala Pro Asp
 1               5                  10                  15

Gly Tyr Val Pro Thr Ser Val Ser Cys Pro Ala Ser Arg Pro Thr Val
                20                  25                  30

Arg Ser Ala Ala Lys Leu Ser Thr Asn Glu Thr Ser Trp Leu Glu Val
            35                  40                  45

Arg Arg Gly Lys Thr Leu Ser Ala Leu Lys Asp Phe Phe Gly His Val
        50                  55                  60

Lys Val Gly Asp Tyr Asp Val Gly Ala Tyr Leu Asp Lys His Ser Gly
65                  70                  75                  80

Asn Ser Ser Leu Pro Asn Ile Gly Ile Ala Val Ser Gly Gly Gly
                85                  90                  95

Trp Arg Ala Leu Met Asn Gly Ala Gly Ala Val Lys Ala Phe Asp Ser
               100                 105                 110

Arg Thr Asp Asn Ala Thr Ala Thr Gly His Leu Gly Gly Leu Leu Gln
           115                 120                 125

Ser Ala Thr Tyr Ile Ser Gly Leu Ser Gly Gly Ser Trp Leu Leu Gly
       130                 135                 140

Ser Ile Tyr Ile Asn Asn Phe Thr Thr Val Asp Lys Leu Gln Thr His
145                 150                 155                 160

Glu Ala Gly Ser Val Trp Gln Phe Gly Asn Ser Ile Ile Glu Gly Pro
               165                 170                 175

Asp Ala Gly Gly Ile Gln Leu Leu Asp Ser Ala Gly Tyr Tyr Lys Asp
           180                 185                 190

Leu Ala Asp Ala Val Asp Gly Lys Lys Lys Ala Gly Phe Asp Thr Thr
       195                 200                 205

Leu Thr Asp Ile Trp Gly Arg Ala Leu Ser Tyr Gln Met Phe Asn Ala
   210                 215                 220

Ser Asn Gly Gly Leu Ser Tyr Thr Trp Ser Ser Ile Ala Asp Thr Pro
225                 230                 235                 240

Glu Phe Gln Asp Gly Asp Tyr Pro Met Pro Phe Val Val Ala Asp Gly
               245                 250                 255

Arg Asn Pro Gly Glu Leu Val Ile Gly Ser Asn Ser Thr Val Tyr Glu
           260                 265                 270

Phe Asn Pro Trp Glu Phe Gly Thr Phe Asp Pro Thr Ile Phe Gly Phe
       275                 280                 285

Val Pro Leu Glu Tyr Leu Gly Ser Lys Phe Glu Gly Gly Ser Leu Pro
   290                 295                 300

Ser Asn Glu Ser Cys Ile Arg Gly Phe Asp Ser Ala Gly Phe Val Ile
305                 310                 315                 320

Gly Thr Ser Ser Ser Leu Phe Asn Gln Phe Leu Leu Gln Ile Asn Thr
               325                 330                 335

```
Thr Ser Leu Pro Ser Phe Ile Lys Asp Val Phe Asn Gly Ile Leu Phe
            340                 345                 350

Asp Leu Asp Lys Ser Gln Asn Asp Ile Ala Ser Tyr Asp Pro Asn Pro
            355                 360                 365

Phe Tyr Lys Tyr Asn Glu His Ser Ser Pro Tyr Ala Ala Gln Lys Leu
        370                 375                 380

Leu Asp Val Val Asp Gly Gly Glu Asp Gly Gln Asn Val Pro Leu His
385                 390                 395                 400

Pro Leu Ile Gln Pro Glu Arg His Val Asp Val Ile Phe Ala Val Asp
                405                 410                 415

Ser Ser Ala Asp Thr Asp Tyr Phe Trp Pro Asn Gly Thr Ser Leu Val
            420                 425                 430

Ala Thr Tyr Glu Arg Ser Leu Asn Ser Ser Gly Ile Ala Asn Gly Thr
        435                 440                 445

Ala Phe Pro Ala Val Pro Asp Gln Asn Thr Phe Ile Asn Leu Gly Leu
        450                 455                 460

Ser Thr Arg Pro Ser Phe Phe Gly Cys Asp Ser Ser Asn Gln Thr Gly
465                 470                 475                 480

Pro Ser Pro Leu Val Val Tyr Ile Pro Asn Ala Pro Tyr Ser Tyr His
            485                 490                 495

Ser Asn Ile Ser Thr Phe Gln Leu Ser Thr Asp Asp Ala Glu Arg Asp
            500                 505                 510

Asn Ile Ile Leu Asn Gly Tyr Glu Val Ala Thr Met Ala Asn Ser Thr
            515                 520                 525

Leu Asp Asp Asn Trp Thr Ala Cys Val Ala Cys Ala Ile Leu Ser Arg
            530                 535                 540

Ser Phe Glu Arg Thr Gly Thr Thr Leu Pro Asp Ile Cys Ser Gln Cys
545                 550                 555                 560

Phe Asp Arg Tyr Cys Trp Asn Gly Thr Val Asn Ser Thr Arg Pro Glu
                565                 570                 575

Ser Tyr Asp Pro Ala Phe Tyr Leu Ala Asp Asn Ser Met Ala Ser Val
            580                 585                 590

Ser Leu Pro Thr Met Leu Ser Thr Val Val Ala Ala Gly Leu Ala Met
            595                 600                 605

Leu Ile Leu Val
    610

<210> SEQ ID NO 17
<211> LENGTH: 664
<212> TYPE: PRT
<213> ORGANISM: Saccharomyces cerevisiae

<400> SEQUENCE: 17

Met Lys Leu Gln Ser Leu Leu Val Ser Ala Ala Val Leu Thr Ser Leu
 1               5                  10                  15

Thr Glu Asn Val Asn Ala Trp Ser Pro Asn Asn Ser Tyr Val Pro Ser
            20                  25                  30

Asn Val Thr Cys Asp Asp Ile Asn Leu Val Arg Glu Ala Ser Gly
        35                  40                  45

Leu Ser Asp Asn Glu Thr Glu Trp Leu Lys Lys Arg Asp Ala Tyr Thr
    50                  55                  60

Lys Glu Ala Leu His Ser Phe Leu Asn Arg Ala Thr Ser Asn Phe Ser
65                  70                  75                  80

Asp Thr Ser Leu Leu Ser Thr Leu Phe Gly Ser Asn Ser Ser Asn Met
```

-continued

```
                    85                  90                  95
Pro Lys Ile Ala Val Ala Cys Ser Gly Gly Tyr Arg Ala Met Leu
                100                 105                 110
Ser Gly Ala Gly Met Leu Ala Ala Met Asp Asn Arg Thr Asp Gly Ala
                115                 120                 125
Asn Glu His Gly Leu Gly Gly Leu Leu Gln Gly Ala Thr Tyr Leu Ala
            130                 135                 140
Gly Leu Ser Gly Gly Asn Trp Leu Thr Ser Thr Leu Ala Trp Asn Asn
145                 150                 155                 160
Trp Thr Ser Val Gln Ala Ile Val Asp Asn Thr Thr Glu Ser Asn Ser
                165                 170                 175
Ile Trp Asp Ile Ser His Ser Ile Leu Thr Pro Asp Gly Ile Asn Ile
                180                 185                 190
Phe Lys Thr Gly Ser Arg Trp Asp Asp Ile Ser Asp Val Gln Asp
                195                 200                 205
Lys Lys Asp Ala Gly Phe Asn Ile Ser Leu Ala Asp Val Trp Gly Arg
            210                 215                 220
Ala Leu Ala Tyr Asn Phe Trp Pro Ser Leu His Arg Gly Gly Val Gly
225                 230                 235                 240
Tyr Thr Trp Ser Thr Leu Arg Glu Ala Asp Val Phe Lys Asn Gly Glu
                245                 250                 255
Met Pro Phe Pro Ile Thr Val Ala Asp Gly Arg Tyr Pro Gly Thr Thr
                260                 265                 270
Val Ile Asn Leu Asn Ala Thr Leu Phe Glu Phe Asn Pro Phe Glu Met
            275                 280                 285
Gly Ser Trp Asp Pro Thr Leu Asn Ala Phe Thr Asp Val Lys Tyr Leu
290                 295                 300
Gly Thr Asn Val Thr Asn Gly Lys Pro Val Asn Lys Gly Gln Cys Ile
305                 310                 315                 320
Ala Gly Phe Asp Asn Thr Gly Phe Ile Thr Ala Thr Ser Ser Thr Leu
                325                 330                 335
Phe Asn Gln Phe Leu Leu Arg Leu Asn Ser Thr Asp Leu Pro Ser Phe
            340                 345                 350
Ile Ala Asn Leu Ala Thr Asp Phe Leu Glu Asp Leu Ser Asp Asn Ser
            355                 360                 365
Asp Asp Ile Ala Ile Tyr Ala Pro Asn Pro Phe Lys Glu Ala Asn Phe
        370                 375                 380
Leu Gln Lys Asn Ala Thr Ser Ser Ile Ile Glu Ser Glu Tyr Leu Phe
385                 390                 395                 400
Leu Val Asp Gly Gly Glu Asp Asn Gln Asn Ile Pro Leu Val Pro Leu
                405                 410                 415
Leu Gln Lys Glu Arg Glu Leu Asp Val Ile Phe Ala Leu Asp Asn Ser
            420                 425                 430
Ala Asp Thr Asp Asp Tyr Trp Pro Asp Gly Ala Ser Leu Val Asn Thr
            435                 440                 445
Tyr Gln Arg Gln Phe Gly Ser Gln Gly Leu Asn Leu Ser Phe Pro Tyr
            450                 455                 460
Val Pro Asp Val Asn Thr Phe Val Asn Leu Gly Leu Asn Lys Lys Pro
465                 470                 475                 480
Thr Phe Phe Gly Cys Asp Ala Arg Asn Leu Thr Asp Leu Asp Tyr Ile
                485                 490                 495
Pro Pro Leu Ile Val Tyr Ile Pro Asn Ser Arg His Ser Phe Asn Gly
                500                 505                 510
```

-continued

```
Asn Gln Ser Thr Phe Lys Met Ser Tyr Ser Asp Ser Glu Arg Leu Gly
        515                 520                 525

Met Ile Lys Asn Gly Phe Glu Ala Ala Thr Met Gly Asn Phe Thr Asp
    530                 535                 540

Asp Ser Asp Phe Leu Gly Cys Val Gly Cys Ala Ile Ile Arg Arg Lys
545                 550                 555                 560

Gln Gln Asn Leu Asn Ala Thr Leu Pro Ser Glu Cys Ser Gln Cys Phe
            565                 570                 575

Thr Asn Tyr Cys Trp Asn Gly Thr Ile Asp Ser Arg Ser Val Ser Gly
        580                 585                 590

Val Gly Asn Asp Asp Tyr Ser Ser Ala Ser Leu Ser Ala Ser Ala
        595                 600                 605

Ala Ala Ala Ser Ala Ser Ala Ser Ala Ser Ala Ser Ala Ser Ala Ser
    610                 615                 620

Ala Ser Gly Ser Ser Thr His Lys Lys Asn Ala Gly Asn Ala Leu Val
625                 630                 635                 640

Asn Tyr Ser Asn Leu Asn Thr Asn Thr Phe Ile Gly Val Leu Ser Val
            645                 650                 655

Ile Ser Ala Val Phe Gly Leu Ile
            660

<210> SEQ ID NO 18
<211> LENGTH: 649
<212> TYPE: PRT
<213> ORGANISM: Torulaspora delbrueckii

<400> SEQUENCE: 18

Met Asn Leu Lys Glu Trp Leu Leu Phe Ser Asp Ala Val Phe Phe Ala
1               5                   10                  15

Gln Gly Thr Leu Ala Trp Ser Pro Ser Asn Ser Tyr Thr Pro Ala Asn
            20                  25                  30

Val Ser Cys Asp Glu Asp Ile Asn Leu Ile Arg Gln Ala Ser Gly Pro
        35                  40                  45

Ser Asp Asn Glu Thr Glu Trp Leu Lys Lys Arg Asp Val Tyr Thr Arg
    50                  55                  60

Glu Ala Leu Arg Ser Phe Leu Asp Arg Ala Thr Ser Asn Phe Ser Asp
65                  70                  75                  80

Ser Ser Leu Val Ser Gln Leu Phe Ser Asn Ala Ser Asp Ile Pro Arg
            85                  90                  95

Ile Ala Val Ala Cys Ser Gly Gly Tyr Arg Ala Met Leu Ser Gly
            100                 105                 110

Ala Gly Met Leu Ala Ala Met Asp Asn Arg Thr Asp Gly Ala Asn Glu
            115                 120                 125

His Gly Leu Gly Gly Leu Leu Gln Ser Thr Thr Tyr Leu Ala Gly Leu
        130                 135                 140

Ser Gly Gly Asn Trp Leu Val Gly Thr Leu Ala Trp Asn Asn Trp Thr
145                 150                 155                 160

Ser Val Gln Asp Ile Val Asn Asn Met Thr Glu Asp Asp Ser Ile Trp
            165                 170                 175

Asp Ile Ser Asn Ser Ile Ile Asn Pro Gly Gly Phe Met Ile Val Thr
            180                 185                 190

Thr Ile Lys Arg Trp Asp His Ile Ser Asp Ala Val Glu Gly Lys Gln
        195                 200                 205

Asp Ala Gly Phe Asn Val Ser Leu Thr Asp Ile Trp Gly Arg Ala Leu
```

-continued

```
            210                 215                 220
Ser Tyr Asn Phe Phe Pro Ser Leu Tyr Arg Gly Val Ala Tyr Thr
225                 230                 235                 240

Trp Ser Thr Leu Arg Asp Val Glu Val Phe Gln Asn Gly Glu Met Pro
                    245                 250                 255

Phe Pro Ile Ser Val Ala Asp Gly Arg Tyr Pro Gly Thr Gln Ile Ile
                260                 265                 270

Asp Leu Asn Ala Thr Val Phe Glu Phe Asn Pro Phe Glu Met Gly Ser
                275                 280                 285

Trp Asp Pro Thr Leu Asn Ala Phe Thr Asp Val Lys Tyr Leu Gly Thr
    290                 295                 300

Lys Val Ser Asn Gly Glu Pro Val Asn Lys Gly Gln Cys Val Ala Gly
305                 310                 315                 320

Tyr Asp Asn Thr Gly Phe Ile Met Gly Thr Ser Ser Ser Leu Phe Asn
                325                 330                 335

Gln Phe Leu Leu Gln Ile Asn Ser Thr Ser Leu Pro Ser Phe Ile Lys
                340                 345                 350

Asn Leu Val Thr Gly Phe Leu Asp Asp Leu Ser Glu Asp Glu Asp Asp
                355                 360                 365

Ile Ala Ile Tyr Ala Pro Asn Pro Phe Lys Asp Thr Ser Tyr Ile Gln
    370                 375                 380

Asp Asn Phe Ser Lys Ser Ile Ser Glu Ser Asp Tyr Leu Tyr Leu Val
385                 390                 395                 400

Asp Gly Gly Glu Asp Asn Gln Asn Ile Pro Leu Val Pro Leu Val Gln
                405                 410                 415

Asp Glu Arg Asn Val Asp Val Ile Phe Ala Leu Asp Asn Ser Ala Asp
                420                 425                 430

Thr Asp Tyr Tyr Trp Pro Asp Gly Ala Ser Leu Val Ser Thr Tyr Glu
                435                 440                 445

Arg Gln Phe Ser Ser Gln Gly Leu Asn Met Ser Phe Pro Tyr Val Pro
    450                 455                 460

Asp Lys Arg Thr Phe Val Asn Leu Gly Leu Ala Asp Lys Pro Ser Phe
465                 470                 475                 480

Phe Gly Cys Asp Ala Gln Asn Leu Thr Asp Leu Asn Tyr Ile Pro Pro
                485                 490                 495

Leu Val Val Tyr Ile Pro Asn Ala Arg His Ser Tyr Asn Ser Asn Thr
                500                 505                 510

Ser Thr Phe Lys Leu Ser Tyr Thr Asp Asp Glu Arg Leu Lys Met Ile
    515                 520                 525

Lys Asn Gly Phe Glu Ala Ala Thr Arg Gly Asn Leu Thr Asp Asp Ser
530                 535                 540

Ser Phe Met Gly Cys Val Ala Cys Ala Val Met Arg Arg Lys Gln Gln
545                 550                 555                 560

Ser Leu Asn Ala Thr Leu Pro Glu Glu Cys Ser Thr Cys Phe Thr Asn
                565                 570                 575

Tyr Cys Trp Asn Gly Thr Ile Asp Asp Thr Pro Val Ser Gly Leu Asp
                580                 585                 590

Asn Ser Asp Phe Asp Pro Thr Ala Ala Ser Ser Ala Tyr Ser Ala Tyr
                595                 600                 605

Asn Thr Glu Ser Tyr Ser Ser Ser Ala Thr Gly Ser Lys Lys Asn
610                 615                 620
```

```
-continued

Gly Ala Gly Leu Pro Ala Thr Pro Thr Ser Phe Thr Ser Ile Leu Thr
625                 630             635                 640

Leu Leu Thr Ala Ile Ala Gly Phe Leu
                645
```